United States Patent [19]

Manz et al.

[11] Patent Number: 5,599,503
[45] Date of Patent: Feb. 4, 1997

[54] DETECTOR CELL

[75] Inventors: Andreas Manz; Elisabeth Verpoorte, both of Basel, Switzerland

[73] Assignee: Ciba-Geigy Corporation, Tarrytown, N.Y.

[21] Appl. No.: 797,500

[22] Filed: Nov. 22, 1991

[30] Foreign Application Priority Data

Nov. 26, 1990 [CH] Switzerland ............... 3741/90

[51] Int. Cl.⁶ .................... G01N 21/29; G01N 21/64
[52] U.S. Cl. .................... 422/82.05; 422/82.08; 422/82.09; 356/246; 356/440
[58] Field of Search ............... 422/68.1, 82.05, 422/82.08, 82.09; 356/432, 436, 440, 246

[56] References Cited

U.S. PATENT DOCUMENTS

| | | | |
|---|---|---|---|
| 3,810,695 | 5/1974 | Shea | 356/73 |
| 4,074,940 | 2/1978 | Tarbet | 356/246 |
| 4,243,883 | 1/1981 | Schwarzmann | 250/343 |
| 4,405,235 | 9/1983 | Rossiter | 356/246 |
| 4,471,647 | 9/1984 | Jerman et al. | 73/23.4 |
| 4,823,168 | 4/1989 | Kamahori et al. | 356/246 |
| 4,908,112 | 3/1990 | Pace | 204/299 R |
| 4,989,974 | 2/1991 | Anton et al. | 356/246 |
| 5,034,194 | 7/1991 | Miller et al. | 356/440 X |

FOREIGN PATENT DOCUMENTS

| | | |
|---|---|---|
| 0089157 | 9/1983 | European Pat. Off. . |
| 0347579 | 12/1989 | European Pat. Off. . |
| 2060865 | 12/1971 | Germany . |
| 0097841 | 4/1989 | Japan ................ 356/440 |
| WO88/01376 | 2/1988 | WIPO . |

OTHER PUBLICATIONS

Yeung et al., Analytical Chemistry, vol. 58, No. 12 (1986) pp. 1237A–1256A.
Xi et al., Analytical Chemistry, vol. 62 (1990) pp. 1580–1585.

Primary Examiner—Robert J. Warden
Assistant Examiner—Theresa T. Snider
Attorney, Agent, or Firm—Kevin T. Mansfield; Marla J. Mathias

[57] ABSTRACT

A miniaturized detector cell (4) having a measuring chamber volume of 25 fl–1 μl is described. In spite of its miniaturized construction, the detector cell has an optical path length of about 0.1–100 mm. The incident measuring light (R) is repeatedly reflected at the inner walls (23, 25, 26) of the interaction region (21) before it leaves the detector cell (4) again. In a preferred manner, the detector cell (4) is manufactured from silicon or quartz by photolithographic means.

18 Claims, 4 Drawing Sheets

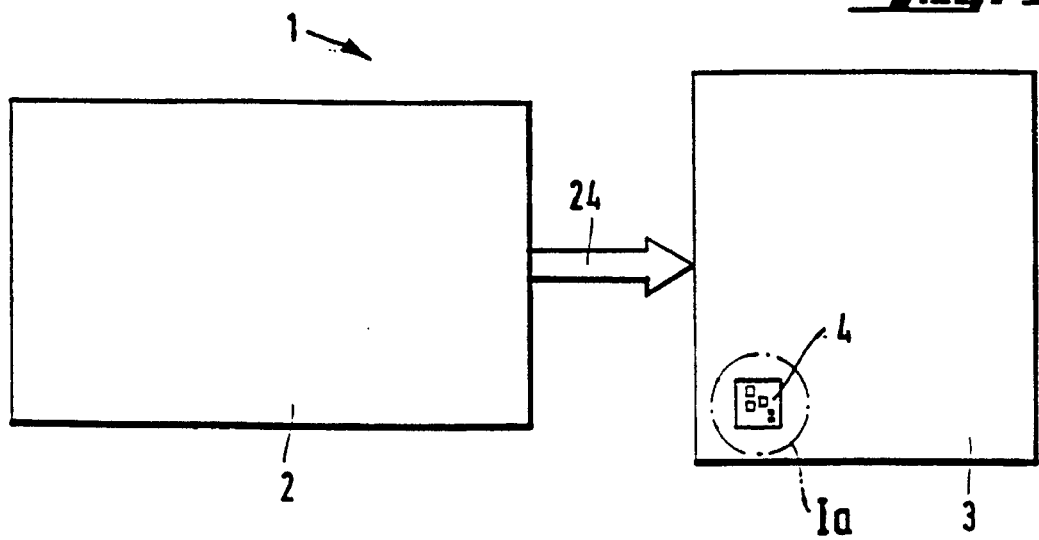
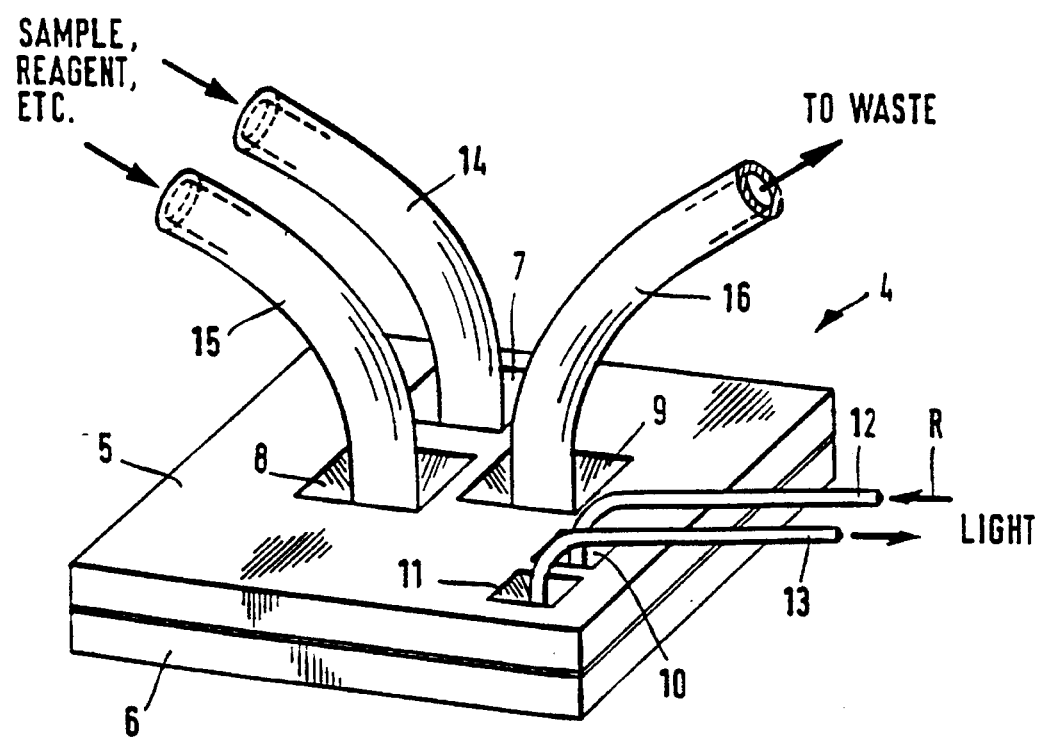

DETECTOR CELL

BACKGROUND OF THE INVENTION

The invention relates to a detector cell, especially for measuring the absorption of ultraviolet and/or visible radiation.

Detector cells are used in analytical chemistry in large number for measuring the absorption of a sample in the ultraviolet (UV) and/or visible region of the electromagnetic spectrum. Where applicable, excited fluorescence, chemiluminescence or absorption in the infrared (IR) region of the spectrum are also measured. In addition to being used in sample measuring techniques, environmental analysis and medical diagnostics, detector cells are increasingly being used for absorption measurements especially also in analytical separation methods, such as, for example, liquid chromatography (LC), capillary electrophoresis (CE), supercritical fluid chromatography (SFC) or flow-injection analysis (FIA). Such detector cells are usually in the form of flow cells. These have an inlet opening for the sample to be analysed, and an outlet opening which is often arranged approximately opposite the inlet opening. A measuring chamber arranged between those openings is usually equipped with two measuring windows lying opposite each other. Radiation is passed in via one of the measuring windows onto the sample flowing through the flow cell and, after passing through the sample, is picked up and detected at the opposing measuring window. Measuring cells of that kind are described, for example, in U.S. Pat. No. 3 810 695 or also in U.S. Pat. No. 4 243 883. They are intended for on-line use in production plants and the like and have a measuring chamber of relatively large volume. These flow cells, however, are not suitable for use in analytical separation methods since, owing to the large volume of the measuring chamber, re-mixing and uncontrollable spreading of the separated components of the sample within the carrier medium would occur.

The desire for a reduction in the measuring volume therefore resulted in the development of so-called flow cuvettes. These are essentially a scaled-down version of the known flow cells. Such cuvettes usually have measuring volumes ranging from some hundreds of nanoliters up to a few milliliters. Measuring cells of this kind are described, for example, in a publication by Edward S. Yeung and Robert E. Synovec in Analytical Chemistrry, vol. 58, No. 12, October 1986, pages 1237A–1256A. Suitable construction of the flow region—approximately Z-shaped in the embodiment described—and somewhat slanting irradiation of the sample in the measuring cell region ensure that the measuring radiation travels as long a path as possible in the sample in order to achieve the greatest possible probability of absorption. Despite those measures, detector cells constructed in that manner do not produce the desired results with the desired resolution and accuracy.

An alternative kind of detector cell is the so-called "on-column" detector. In these detector cells, a piece of a capillary tube, or the capillary tube of the mentioned analysis system itself, is used as the boundary for the measuring volume. A measuring cell of this kind is described, for example, in EP-A-0 326 511. It comprises a capillary tube which is fastened in a two-part holding device. The measuring light is introduced perpendicular to the axis of the capillary tube through openings provided for that purpose in the holding device, and the transmitted portion of the measuring light is picked up again and detected at the opposite side of the capillary tube. Usually, the measuring light of a source of measuring light arranged outside the measuring cell is supplied to the capillary tube via fibre-optical light guides and is also conveyed away in that manner. The sources of measuring light used are conventional spectroscopic light sources or also coherent light source lasers. Although the volumes of the measuring region in such "micro"-flow cells are very small, being typically in the range of a few nanolitres, owing to the short interaction path, which, of course, substantially corresponds to the internal diameter of the capillary tube used, restraints are placed on the detection limit (defined as the smallest measurable concentration of the eluted sample molecule). The internal diameters of the capillary tubes are typically about from 10 µm to 50 µm.

In order to remedy this shortcoming in the so-called "on-column" detectors, it is proposed by Xiaobing Xi and Edward S. Yeung in Analytical Chemistry, 1990, 62, pages 1580–1585 or also in EP-A-0 089 157 that the measuring light of a laser source be passed through the capillary tube in the direction of flow. In this manner, the interaction path is lengthened by a factor of up to 1000 as compared with the method in which the light is introduced perpendicular to the axis of the capillary tube.

In this proposed method, however, not only is the measuring light attenuated as it passes through the relatively long capillary tube owing to absorption by the sample, but scattering processes occur in the capillary tube and often portions of the measuring light are absorbed by the wall of the capillary tube, which accordingly falsities the result of the measurement. The trend in analytical separation methods, however, such as, for example, LC, CE or SFC which have already been mentioned above, is towards smaller sample volumes and, accordingly, especially also smaller volumes of the measuring chamber or the measuring region of the detector cells. For example, in separation methods, capillary tubes having a diameter of only about 5 µm are used. In biotechnological applications, it is possible in this manner to detect extremely small amounts of a sample, even in the range as small as individual cells. If one assumes that, in the case of separating columns having capillary tube diameters of about 1 mm, the volume of the measuring chamber of the detection cell should be less than 10 µl in order to avoid undesired spreading and re-mixing of the separated substances, it will be appreciated that upon changing to capillary tube diameters of 10 µm or less, the volume of the measuring chamber of the detector cell should be in the range of about 1 nl or less.

Since the detector cells known hitherto either are not designed for such small volumes of the measuring chamber or have too poor a detection limit owing to the short interaction paths of the measuring light with the sample to be analysed, or give false results owing to scattering processes in the capillary tube or absorption in the capillary tube wall, it is desired to provide a detector cell that, on the one hand, exhibits the necessary small volume of the measuring chamber and, on the other hand, has a sufficiently long interaction path of the measuring light with the sample. The detector cell is to be easy to use and, especially, is also to be capable of being used in miniaturised separation apparatus. Apart from having as compact a construction as possible, the detector cell is to be capable of being manufactured as simply, as reproducibly and as economically as possible. The measuring chamber of the detector cell is not to absorb the measuring light. The length of the interaction path of the measuring light with the sample —the optical path length— is to be reproducible. In addition, there is also a desire for a small detector cell that allows a continuous measuring process. All of these objects and still further objects are achieved by a detector cell according to the present invention.

BRIEF DESCRIPTION OF THE DRAWINGS

The detector cell according to the invention is described in detail below with reference to an embodiment shown schematically in the drawings, in which FIG. 1 shows an analytical flow-injection analysis and/or separation system having a detector cell according to the invention, FIG. 1a shows the detector cell Ia of FIG. 1, enlarged.

DETAILED DESCRIPTION OF THE INVENTION

Figure 2:
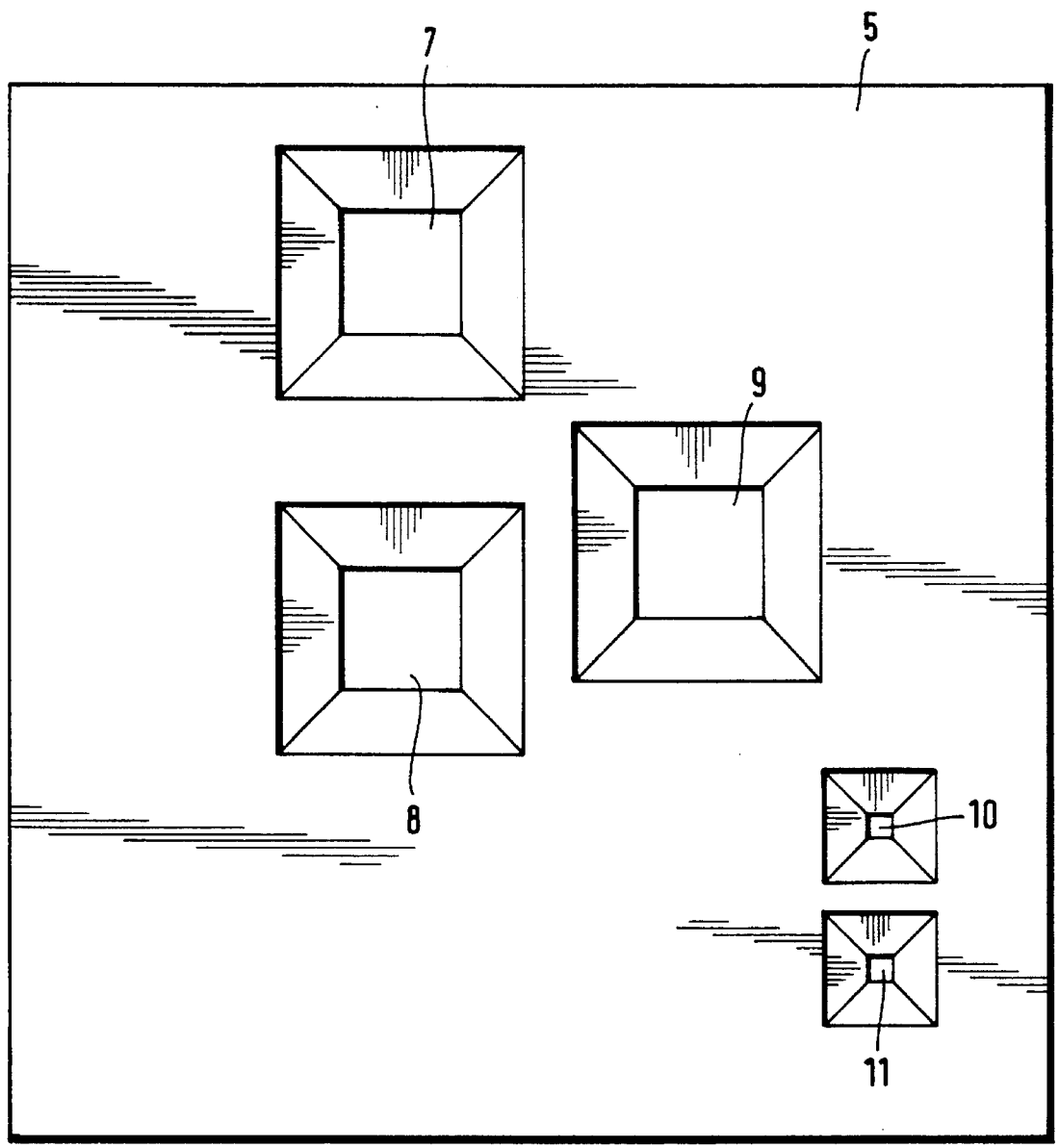
FIG. 2 shows the lid part of the detector cell in plan view.

An analytical system shown by way of example in FIG. 1 for use in liquid chromatography (LC), capillary electrophoresis (CE), supercritical fluid chromatography (SFC) or flow-injection analysis (FIA) has the overall reference numeral 1. It substantially comprises a flow-injection analysis and/or separation station 2 and a detection system 3. The flow-injection analysis and/or separation station 2 and the detection system 3 may, as shown, be two separate constructional units, which are combined via lines 24, but may, of course, also be combined to form a single device. In addition to containing the customary components, such as, for example, a source of measuring light, photoelectric transducers, preferably electronic recording devices, pumps etc. (none of which is shown), the detection system 3 also comprises a detector cell 4 according to the invention. The detector cell 4 is preferably constructed in two parts. It comprises a base part 6 and a lid part 5. Inlet lines 14, 15, preferably capillary tubes, for the sample and any further reagents and the like, and an outlet line 16 for the sample or the sample/reagent mixture lead to connection openings in the lid part 5. Two fibre-optical light guides 12, 13 lead to connection openings provided for that purpose in the lid part 5 and serve to supply and remove the measuring light.

FIG. 2 shows the lid part 5 on a larger scale. The connection openings 7, 8 and 9 for the capillary tubes 14, 15, 16 through which the sample and, where appropriate, any further reagents is(are) introduced into or removed from the detector cell 4 will be seen clearly. The connection openings 7, 8, 9 are preferably constructed as plug-in openings in such a manner that, when plugged in, a respective capillary tube 14, 15 or 16 sits firmly without additional fixing means. The capillary tubes preferably have external diameters of from about 50 μm to about 1000 μm. In particular, the cross-section of the plug-in openings 7, 8, 9 may, as shown, taper downward across the height of the lid part 5 so that, as shown in the plan view of FIG. 2, a frustopyramidal shape of the openings is produced. In the case of substantially circular openings, a frustoconical shape of the latter will be produced. The smallest cross-section of the plug-in openings 7, 8, 9 should approximately correspond to the internal cross-section of the capillary tubes 14, 15, 16 used. The plug-in openings 10 and 11 for the respective fibre-optical light guides 12 and 13 are of analogous construction but usually have a smaller cross-section. Here too, it is possible to see clearly the cross-section of the opening tapering from the top downward across the height of the lid part 5. As in the case of the plug-in openings 7, 8, 9 for the capillary tubes 14, 15, 16, the smallest cross-section in the case of the plug-in openings 10, 11 for the fibre-optical light guides 12, 13 should approximately correspond to the cross-section of the light-conducting core of the fibre. The plug-in openings 7, 8, 9, 10, 11 may alternatively, however, be tapered in steps or have a constant diameter.

Figure 3:
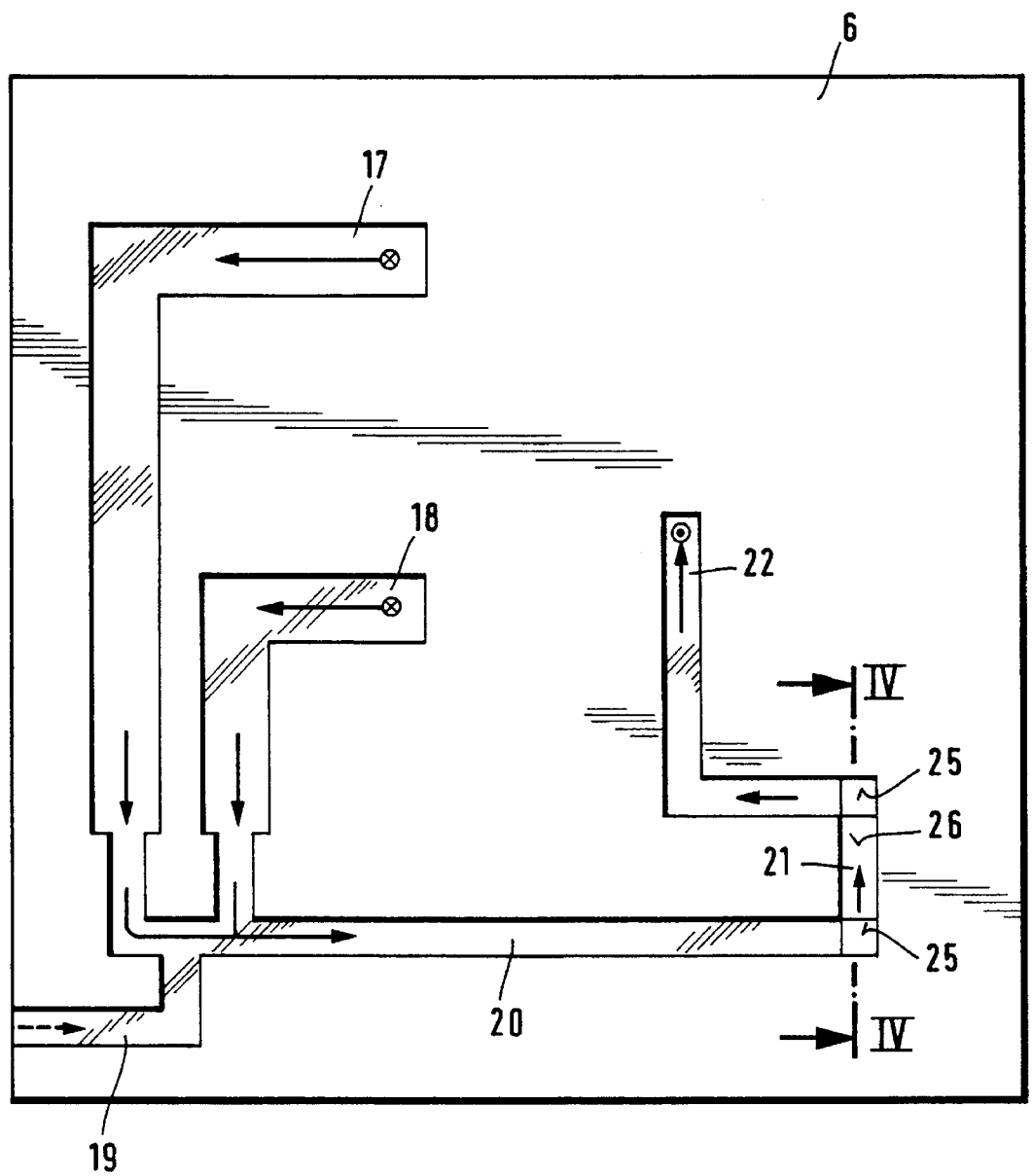
FIG. 3 shows the base part of the detector cell in plan view.

The associated base part 6 shown in FIG. 3 has a plurality of channels which are connected to one another. When the detector cell 4 is in the assembled state, two inlet channels 17 and 18 are in communication with the respective connection openings 7 and 8 for the capillary tubes 14 and 15 and lead to a channel piece 20. As shown, a further channel 19 may lead to the channel piece 20 and form on the base part 6 a direct connection of the system of channels to the outside. The channel piece 20 leads to a channel piece 21 which constitutes the interaction path which has yet to be described in detail. Finally, another channel piece 22 is connected which, when the detector cell 4 is in the assembled state, is in communication with the plug-in opening 9 for the outlet capillary tube 16. According to the view shown in FIG. 3, the inlet channels 17 and 18 are of larger dimensions than is the channel system 20-21-22. Constructed in this manner, the inlet channels 17 and 18 form a kind of reservoir for the sample, which is usually pumped through the detector cell 4 by means of peristaltic pumps, and for any additional reagents. Owing to the smaller cross-section of the channel system 20-21-22, a slight pressure builds up in the inlet channels 17, 18, which ensures continuous transport of the media through the detector cell 4 even when the pump output fluctuates slightly. In addition, owing to this buffer function of the inlet channels 17, 18 of larger cross-section, shock waves produced in the transported media owing to the movement of pistons or diaphragms of the pumps are absorbed to a large extent. The channel 19 leading to the outside, on the other hand, has the same cross-section as the channel system 20-21-22. It is used, for example, to introduce the sample when such effects are of no significance or do not occur at all owing to different methods of transport for the sample, for example by means of electrical fields.

Figure 4:
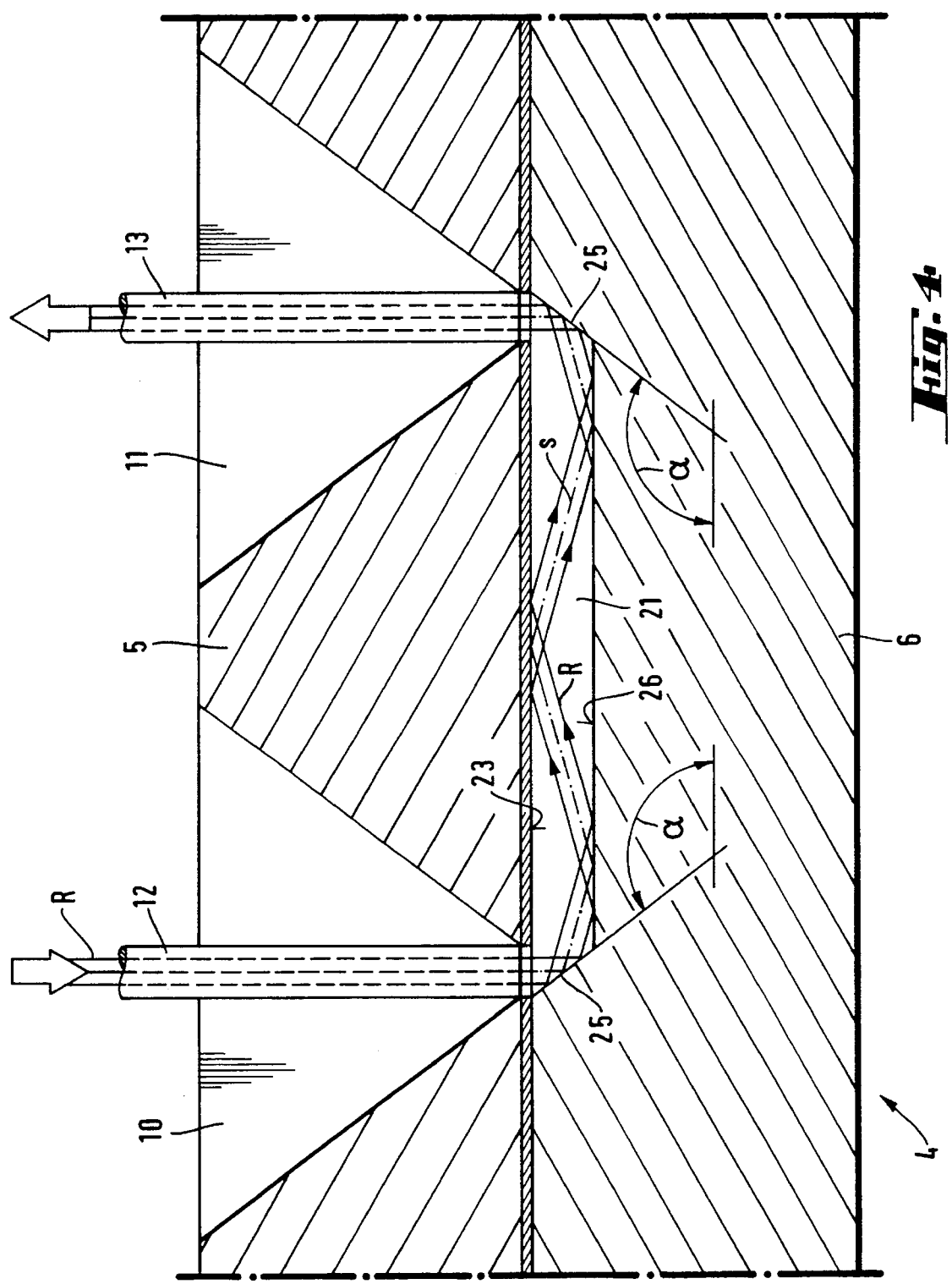
FIG. 4 shows a section through the interaction path of an assembled detector cell along the section line IV—IV in FIG. 3.

FIG. 4 shows a view of the channel piece 21 in section along the section line IV—IV of FIG. 3. In particular, this channel piece, which, of course, forms the actual interaction region for the measuring light R with the sample to be investigated, is shown in the assembled state of the detector cell 4. It will clearly be seen that the channel piece 21, which extends preferably in a straight line, is in communication at its two ends with the plug-in openings 10 and 11 for the two fibre-optical light guides 12 and 13. The already mentioned shape of the plug-in openings 10 and 11 which tapers in cross-section from the top downward across the height of the lid part 5 can also be seen clearly. Two plugged-in fibre-optical light guides 12 and 13 are indicated. The construction of the channel piece 21, the actual interaction region, is such that the end-face side walls 25 of the channel piece 21 form with the base 26 of the channel piece 21 an angle α of from about 90° to about 180°, especially from about 110° to about 150°. The longitudinal side walls of the channel piece 21 are also usually inclined with respect to the channel base at a similar angle.

FIG. 4 also shows that the underside of the lid part 5, that is, the side facing the channel base 26, is coated with a reflective layer 23 at least in the region of the channel portion 21 which serves as the interaction region. The end-face side walls 25 of the channel piece 21 and the channel base 26 also have surfaces with good reflection properties. This can similarly be achieved by a suitable coating. It is also possible, however, to use a material that has very good reflection properties for the manufacture of the base part 6.

The volume of the channel piece 21 which is defined at the top by the coated underside of the lid part 5 is preferably from about 25 fl to about 1 μl. With a channel depth of from about 0.5 μm to about 500 μm, this gives a cross-sectional area of the channel piece 21 of from about 0.25 μm$^2$ to about 0.25 mm$^2$. Measuring light R which is introduced via the optical fibre 12 plugged into the connection opening 10, impinges on the inclined end-face side wall 25 at the inlet end of the channel piece 21 and is reflected from there to the channel base 26. In accordance with the laws of reflection, the measuring light R is reflected from the channel base 26 to the reflective layer 23 on the underside of the lid part 5, from there to the channel base 26 again and so on. After being reflected several times, the measuring light R reaches the second end-face side wall 25 of the channel piece 21 and is reflected from there towards the connection opening 11 and coupled into the plugged-in optical fibre 13 and guided away. As a result of these multiple reflections the interaction path of the measuring light R is significantly lengthened: in particular, there are obtained in this manner with channel piece lengths of from about 100 μm to about 5 cm and with a channel depth of from about 0.5 μm to about 500 μm, interaction paths, that is to say optical lengths, of from about 0.1 mm to about 10 cm.

In the application of the detector cell 4, a sample, and, where appropriate, further reagents, is(are) introduced into the detector cell 4 via the connection opening 7, 8, 9 or 19. A preliminary run ensures that the detector cell is filled. The fibre-optical light guides 12 and 13 can be varied in the funnel-shaped plug-in openings 10 and 11 with regard to the position of their light entry and exit ends relative to the inlet and outlet end-face side walls 25 of the channel piece 21, thus compensating for refraction effects of the liquid sample. In particular, the angle at which the measuring light R is introduced is varied in this manner until a maximum signal level is achieved. This "calibration" may also be performed, of course, by altering the position of the light exit optical fibre 13, or also by altering the position of the two fibre-optical light guides 12 and 13. After these preparatory measures, the absorption measurement proper can be carried out.

The lid part 5 and the base pan 6 are preferably manufactured from monocrystalline silicon. The selection of this material permits the use of proven manufacturing techniques such as are known, for example, from the semi-conductor industry. In this manner, it is possible to produce the individual channels by photolithographic means, by using masking techniques and, for example, wet-chemical or plasma etching steps. The use of these technologies known from semi-conductor production permits the reproducible manufacture of a large number of identical components. The reflective coating on the surfaces of the channels, or at least of the channel piece 21 serving as the interaction region, is produced by oxidation of the monocrystalline silicon, forming a SiO$_2$ layer of precisely definable thickness. The underside of the lid part also can easily be provided with a reflective layer by oxidation. The connection openings 7–11 can similarly be produced by photolithographic means by etching quite specific regions of the monocrystalline silicon. Alternatively, however, these openings could, of course, be drilled using a laser. It goes without saying that monocrystalline silicon is not the only material suitable for the manufacture of the detector cell 4. It is, of course, also possible to use materials similar to silicon from main group IV of the Periodic Table of the Elements and also so-called III–V–combination materials. It is also possible to use quartz or polycrystalline materials and even amorphous silicon compounds and compounds similar thereto. Instead of using photolithographic processing methods to produce the plug-in openings in the lid part and the channels in the base part, these could also be produced by means of micro-mechanical machining methods. The reason for the special preference for silicon, especially monocrystalline silicon, resides in its ready availability, in the proven processing and machining techniques for silicon and in its very good chemical resistance. Monocrystalline silicon is supplied in wafers of up to 8 inches diameter. If one considers that the dimensions of the detector cell 4 according to the invention provide for a length of from about 3 mm to about 55 mm and a width of only from about 3 mm to about 10 mm, it will readily be appreciated that, in this manner, a large number of identical components can be produced in a very economical manner on only one wafer of monocrystalline silicon. The finished components (lid parts and base parts) then need only to be sawn from the wafer. The thickness of silicon wafers is usually from about 50 μm to about 1000 μm. If one considers that this thickness determines the height of the individual component, lid part or base pan, after processing and separation into individual components, this results in assembled detector cells having an overall height of only from about 150 μm to about 2000 μm. The lid pan 5 and the base pan 6 of the detector cell 4 are usually adhesively bonded or otherwise permanently joined to each other. Alternatively, however, they could be held pressed one on top of the other in a common holding device. The construction according to the invention of the detector cell has a sufficiently small measuring chamber volume (volume of the interaction region) without its entailing a deterioration in the detection limit as compared with known, conventional cells. Owing to the miniaturised construction, the detector cell according to the invention furthermore satisfies the prerequisite for integration in miniaturised analysis systems such as are or will be used in modern capillary-separation and micro-separation techniques today or in the future.

What is claimed is:

1. A detector cell for measuring the absorption of ultraviolet and/or visible radiation in substantially liquid samples, comprising:

a) base pan with a groove channel system including a channel piece which is defined by a base region surface and a top face surface, both of which surfaces reflect the measuring radiation, and b) a lid part, including an inlet opening and outlet opening for the introduction and removal of a sample, and an entry opening and exit opening for ultraviolet and/or visible measuring radiation, wherein said lid part and base part are cooperatively aligned to define an interaction region wherein the sample may be introduced from the inlet opening, pass through the groove channel system and exit the outlet opening, and also wherein the measuring radiation may be introduced from the entry opening, pass through the channel piece of said groove channel system and exit the exit opening.

2. A detector cell according to claim 1, wherein said channel piece has side walls which form with said base region surface of said channel piece an angle of from about 90° to less than 180°, and have a surface that reflects said measuring radiation.

3. A detector according to claim 2, wherein said angle is from about 110° to about 150°.

4. A detector cell according to claim 1, wherein said channel piece has a volume of from about 25 fl to about 1 µl.

5. A detector cell according to claim 1, wherein said openings in the lid part are constructed as plug-in openings in such a manner that their cross-section tapers across the height of said lid part from the upper side of said lid part towards its underside.

6. A detector cell according to claim 5, wherein said inlet and outlet openings are constructed to receive capillary tubes having external diameters form about 50 µm to about 1000 µm.

7. A detector cell according to claim 6, wherein the smallest cross-section of said inlet and outlet openings approximately corresponds to the internal cross-section of said capillary tubes used.

8. A detector cell according to claim 1, wherein the entry and exit openings in said lid part for said measuring light are constructed as plug-in openings for fibre-optical light guides in such a manner that their cross-section tapers across the height of said lid part towards its underside.

9. A detector cell according to claim 8, wherein the smallest cross-section of said fibre-optical light guide plug-in openings approximately corresponds to the core of the light-conducting optical fibres.

10. A detector cell according to claim 1, wherein said channel piece has a cross-sectional area of from about 0.25 µm$^2$ to about 0.25 mm$^2$ with a channel depth of from about 0.5 µm to about 500 µm.

11. A detector cell according to claim 10, which has an optical path length of about 0.1–100 mm.

12. A detector cell according to claim 1, wherein the length of said channel piece is from about 0.1 mm to about 50 mm.

13. A detector cell according to claim 1, wherein said base part and/or said lid part is made of crystalline material or compound of elements of Groups III, IV and V of the Periodic Table of the Elements.

14. A detector cell according to claim 13, wherein said lid and/or base parts are made of monocrystalline silicon wafers of from about 50 µm to about 1000 µmm in thickness.

15. A detector cell according to claim 13, wherein said cyrstalline material or compound of elements of Groups III, IV and V of the Periodic Table of the Elements is glass.

16. A detector cell according to claim 1, wherein said interaction region includes an inlet channel in said base part which is in communication with the inlet opening in the lid part and which leads to the groove channel system, and an outlet channel in said base part which leads from the groove channel system and is in communication with the outlet opening in the lid part.

17. A detector cell according to claim 11, wherein said inlet channel has a larger cross-sectional area than said groove channel system.

18. A detector cell according to claim 1, wherein said detector cell has a length of from about 3 mm to about 55 mm, a width of from about 3 mm to about 10 mm and a height of from about 150 µm to about 2000 µm.

* * * * *